United States Patent [19]

Harris et al.

[11] 3,944,391
[45] Mar. 16, 1976

[54] IN VITRO PROCESS FOR DETECTING ENDOTOXIN IN A BIOLOGICAL FLUID

[75] Inventors: Nick S. Harris; Robert Feinstein, both of Galveston, Tex.

[73] Assignee: Preventive Systems, Inc.

[22] Filed: Dec. 27, 1974

[21] Appl. No.: 536,834

[52] U.S. Cl............ 23/230 B; 195/103.5 R; 210/24
[51] Int. Cl.² C12K 1/00; G01N 31/06; G01N 33/16
[58] Field of Search............... 23/230 B; 210/24; 195/103.5 R

[56] References Cited
UNITED STATES PATENTS 3,770,631  11/1973  Fekete .............................. 210/24
3,794,584  2/1974  Kunin ............................... 210/24

OTHER PUBLICATIONS
Chemical Abstracts, 72:64863c (1970).
Chemical Abstracts, 78:13536q (1973).

*Primary Examiner*—Morris O. Wolk
*Assistant Examiner*—Sidney Marantz
*Attorney, Agent, or Firm*—Pravel & Wilson

[57] ABSTRACT

An in vitro process for detecting the presence of endotoxin in a biological fluid such as a parenteral fluid, whole blood, and the like, wherein amebocyte lysate from the hemolymph of the horseshoe crab, *Limulus polyphemus*, is intimately contacted with and incubated in the presence of a synthetic plastic polymer capable of adsorbing endotoxin which has previously been contacted with the biological fluid. The presence or absence of a gelation reaction in the amebocyte lysate is then observed. The presence of a gelation reaction determines the presence of endotoxin in the biological fluid.

8 Claims, No Drawings

IN VITRO PROCESS FOR DETECTING ENDOTOXIN IN A BIOLOGICAL FLUID

BACKGROUND OF THE INVENTION

This invention relates to an improved in vitro process for assaying for the presence of endotoxin in a biological fluid including the blood of animals and parenteral fluids such as serum, plasma, whole blood, albumins, dextrose solutions, and the like.

Generally speaking, endotoxin is a complex lipopolysaccharide material derived from gram-negative bacilli that is known to produce a wide variety of striking pathophysiological reactions in animals. For many years it was believed that the material was contained within gram-negative bacilli cells and was released only upon disintegration of the cell walls. Hence, the material was termed endotoxin. Recent studies, however, have shown that endotoxin is localized at the cell surface of gram-negative bacilli and may be present with viable and killed cells as well as in a free from within a liquid medium.

Endotoxin has been identified as a direct and contributory cause of death of many hospitalized patients. More particularly, endotoxin is known to cause febrile reactions in animals with symptoms of extremely high fever, vasodilation, diarrhea, and the like and, in extreme cases, fatal shock. It is also known that endotoxin causes leucocytosis, deleterious changes in carbohydrate and protein metabolism and widespread intravascular clotting by fibrin formation.

Studies have shown that endotoxemia in animals may be caused by or is associated with gram-negative bacilli primary and secondary infections and/or the employment of intravenous apparatus or solutions contaminated with gram-negative bacilli or endotoxin. The occurrence of endotoxemia rom the use of endotoxin-contaminated intravenous or parenteral solutions has recently been recognized as a particular problem in modern hospitals. For these reasons, a considerable amount of research has been, and is presently being conducted, to develop a simple, rapid, positive process for detecting the presence of endotoxin in parenteral fluids and in the blood of animals.

There are several procedures known for detecting the presence of endotoxin in many types of biological fluids. More particularly, there are several known bioassay procedures for detecting endotoxin which take advantage of one or more of the biologic effects or the antigenic composition of endotoxin through the use of experimental animals. For example, one of the most widely accepted bioassays for endotoxin is the rabbit pyrogenicity test which is currently used to satisfy Federal Drug Administration requirements for parenteral solutions and biologic products designed for intravenous injection in man. The rabbit pyrogenicity test is carried out by injecting a biological fluid being tested into three or more preconditioned rabbits and continuously monitoring the rectal temperatures of the injected rabbits for at least 3 hours following the injection. Biological fluids contaminated with endotoxin cause febrile reactions in the test rabbits with increased rectal temperatures being observed. In addition, several bioassay procedures for detecting endotoxin have been described which utilize the lethal effects of endotoxin in test animals.

However, known bioassay procedures suffer from several disadvantages. Known bioassay procedures not only require extensive amounts of time but are also relatively difficult to perform. Moreover, such procedures have not been found to be particularly sensitive for detecting the presence of endotoxin and suffer in reliability in view of all the variabilities encountered through the required use of intact test animal systems.

Several in vitro assay procedures for detecting endotoxin in biological fluids are also known. For example, D. K. Heilman and R. C. Bast, Jr., in "J. Bacteriol." 93: 15–20 (1967), disclose an in vitro assay process for detecting endotoxin through the inhibition of macrophage migration by endotoxin. A process for determining the presence of endotoxin in parenteral fluids by the use of membrane filtration has been described by S. Marcus in "Bull. Parenteral Drug Ass." 18:18–24 (1964). However, studies have shown that such in vitro methods are no more sensitive in detecting the presence of endotoxin than many of the aforementioned bioassay procedures and exhibit no significant improvement in reliability.

Several in virto procedures have recently been described for the detection of endotoxin in certain biological fluids by the use of amebocyte lysate from the hemolymph of the horseshoe crab, Limulus polyphemus. Studies have shown that the amebocyte lysate of Limulus crabs is extremely sensitive to endotoxin and coagulates in its presence in a gelation reaction. It has been amply demonstrated that the degree of gelation or coagulation of the amebocyte lysate is quantitative to the amount of endotoxin present. Further, it has been found that the amebocyte lysate is so sensitive to endotoxin as to detect as little as 0.1 ng of endotoxin present in 1 ml of fluid.

Generally, in vitro procedures for detecting the presence of endotoxin in biological fluids employing the amebocyte lysate of Limulus crabs include admixing a sample of the biological fluid with the lysate, incubating the admixture for a predetermined period of time at a predetermined temperature, and observing and grading the degree of gelation of the lysate. Examples of particular procedures employing the Limulus lysate test for detecting endotoxin in a variety of parenteral fluids are described in the following publications: R. R. Rojas-Corona et al. "The Limulus Coagulation Test for Endotoxin: A Comparison with Other Assay Methods," Proc. Soc. Exp. Biol. Med. 132:599–601 (1969); J. F. Cooper et al. "Quantitative Comparison of In Vitro and In-Vivo Methods for the Detection of Endotoxin," J. Lab. Clin. Med. 78:138–147 (1971); and J. F. Cooper et al. "The Limulus Test for Endotoxin (Pyrogen) in Radiopharmaceutical and Biologicals," Bull. Parenteral Drug Ass. 26:153–162 (1972).

Processes have also been described employing the amebocyte lysate of Limulus crabs for detecting endotoxin in human blood. However, such known procedures require extensive treatment of the blood or blood components, such as plasma, prior to testing with the Limulus lysate to remove certain inhibitors that prevent the detection of endotoxin. For example, J. Levin et al. in "Detection of Endotoxin in Human Blood and Demonstration of an Inhibitor," J. Lab. Clin. Med. 75:903–911 (1970), describe a process for detecting endotoxin in human blood by the use of Limulus amebocyte lysate which includes initial treatment of blood plasma containing endotoxin with a 1:4 ratio of chloroform to plasma for a period of 1 hour to remove certain endotoxin inhibitors in the plasma prior to incubation with the Limulus lysate.

R. B. Reinhold et al, in "A Technique for Quantitative Measurement of Endotoxin in Human Plasma," Proc. Soc. Exp. Biol. Med. 137:334-340 (1970), describe the use of a pH shift method of plasma treatment to retard endotoxin binding by plasma proteins in an in vitro process for detecting endotoxin employing Limulus amebocyte lysate.

We have now discovered an improved in vitro process for detecting the presence of endotoxin in the blood of an animal by the use of amebocyte lysate of Limulus crabs which does not require extensive treatment of the blood or any of its components to remove certain plasma inhibitors that was heretofore required in known processes. The process of our invention can be carried out rapidly and simply with no adverse affect on the apparent sensitivity and specificity of Limulus amebocyte lysate to endotoxin. The process of the invention may also be employed for the detection of endotoxin in any type of biological fluid, including parenteral fluids.

SUMMARY OF THE INVENTION

The present invention is an improved in vitro process for detecting the presence of endotoxin in a biological fluid which comprises intimately contacting amebocyte lysate from the hemolymph of the horseshoe crab, *Limulus polyphemus*, with a non-ionogenic hydrophobic non-polar aliphatic synthetic plastic polymer capable of adsorbing endotoxin which has previously been intimately contacted with a biological fluid, incubating the amebocyte lysate in the presence of the synthetic plastic polymer and observing the presence or absence of a gelation reaction in the amebocyte lysate. The observation of a gelation reaction in the amebocyte lysate confirms the presence of endotoxin in the biological fluid to which the synthetic polymer capable of adsorbing endotoxin has previously been intimately contacted with. The inventive process provides a rapid, simple procedure for detecting the presence of endotoxin in biological fluids and is particularly useful for assaying for the presence of endotoxin in whole blood without previous treatment of the blood.

DETAILED DESCRIPTION OF THE INVENTION

The process of the present invention is carried out by initially intimately contacting a biological fluid with a non-ionogenic non-polar hydrophobic aliphatic synthetic plastic polymer capable of adsorbing endotoxin in accordance with the process described in U.S. patent application Ser. No. 536,833, by Nick S. Harris, co-inventor herein, entitled "Process for Removing Endotoxin from Biological Fluids" and filed on even date with this application. More particularly, as described in said co-pending application Ser. No. 536,833, types of synthetic plastic polymer that have been found capable of adsorbing endotoxin include substantially crystalline, non-polar aliphatic hydrocarbon thermoplastic polymers, fluorocarbon polymers, silicone elastomers, and mixtures thereof. Experiments have shown that when a biological fluid contaminated with endotoxin is contacted with these types of polymers, the endotoxin is readily removed from the liquid media, adsorbed by and bound to the synthetic plastic polymer surface and is not readily removed from the polymer surface by simple washing. These types of polymers that have been discovered to have an affinity for and are capable of adsorbing endotoxin are generally aliphatic saturated polymers which are non-ionogenic, substantially non-polar and hydrophobic. Moreover, many of these polymers are classified as crystalline, isotactic polymers.

The substantially crystalline non-polar aliphatic hydrocarbon thermoplastic polymers preferably employed for intimate contacting with a biological fluid include the poly-$\alpha$-olefins, such as polyethylene, polypropylene, and the higher homologue polymers. Any commercially available type or grade of poly-$\alpha$-olefin may be employed in substantially any molecular weight commercial formulation. The polymers may include inert compatible fillers and/or colorants with no adverse affect on their capability of adsorbing endotoxin. Moreover, copolymers may be employed. Examples of particular commercially available poly-$\alpha$-olefins that have been found useful include high density polyethylene, low density polyethylene, and isotactic polypropylene, to name a few.

Fluorocarbon polymers have also been found to have an affinity for endotoxin and may be employed. As known, fluorocarbon polymers are highly crystalline, hydrophobic, non-ionogenic and substantially non-polar thermoplastics. Any commercially available fluorocarbon polymer material may be employed for intimate contacting with a biological fluid, including those substituted with other halogen groups, such as chlorine, and those formulated with inert filler or colorant ingredients. Types of fluorocarbon polymers that have been found to be particularly useful include tetra-fluoroethylene polymers, fluoronated ethylene-propylene polymers and modified copolymers of tetrafluoroethylene and ethylene. These polymers are readily available commercially in a variety of grades. For example, fluoronated ethylene-propylene polymers are sold by E. I. du Pont de Nemours & Co., Inc. under the trademark "TEFLON FEP". Modified copolymers of tetrafluoroethylene and ethylene are also sold by E. I. du Pont de Nemours & Co., Inc. under the trademark "TEFZEL".

In addition, any type of silicon elastomer may be employed for contacting with a biological fluid suspected of being contaminated with endotoxin. Silicone elastomers are classified as thermosetting cross-linked synthetic polymers and are normally quite resilient. Thus, their physical characteristics are somewhat different from the crystalline non-polar aliphatic hydrocarbon polymers and fluorocarbon polymers, mentioned hereinabove. Yet, experiments have shown that silicone elastomers have an affinity for endotoxin and are capable of adsorbing it from a liquid medium. Types of silicone elastomers that are particularly useful in the process of the invention include the high molecular weight linear poly(alkylsiloxane) that are cured by crosslinking linear or slightly branched siloxane chains having reactive silanol end groups. These silicone elastomers are generally referred to in the art as room-temperature vulcanizing silicone elastomers and are readily available commercially. Examples of suitable silicone elastomers include the RTV 732 and 108 silicone elastomers sold by Dow Corning Co., which contain dimethyldichlorosilane and crosslinking agents that cure by cross-linking when exposed to atmospheric moisture. Another suitable silicone elastomer is medical grade silastic sold by Dow Corning Co. which is cross-linked and cured at room-temperature by the addition of stannous octoate. These silicone elastomers are employed after they have been cured or cross-linked to form solidified materials.

The synthetic plastic polymers capable of adsorbing endotoxin may be contacted with the biological fluid suspected of being contaminated with endotoxin in any conventional manner so as to provide intimate contact therewith. Preferably, the synthetic polymer is employed in particulated form, such as beads, granules or chips so as to provide increased polymer surface area and the contacting is carried out by passing the biological fluid through a column containing the particulated synthetic polymer. In addition, if desirable, the biological fluid may be incubated in the presence of the synthetic polymer material at a temperature within the range of from about room-temperature to about 40° C. for a time period of from about 10 minutes to about 2 hours. However, incubation and contact time have not been found to be critical in regard to the capability of the synthetic plastic polymer to adsorb endotoxin.

In accordance with the present invention, the synthetic plastic polymer initially contacted with a biological fluid suspected of being contaminated with endotoxin is removed from contact with the biological fluid and intimately contacted with amebocyte lysate of the horseshoe crab, *Limulus polyphemus*. Surprisingly, endotoxin adsorbed by the synthetic plastic polymer from the biological fluid is capable of causing a gelation reaction in the amebocyte lysate.

Limulus amebocyte lysate employed in the process of the invention may be obtained by lysing amebocyte cells of the hemolymph of *Limulus polyphemus* crabs in accordance with any process known in the art. Several amebocyte lysing methods have been described in the literature. For example, amebocyte lysate may be obtained by lysing washed amebocyte cells by freezing and thawing in dry ice and acetone as described by J. Levin and F. B. Bang in "Clottable Protein in Limulus: Its Localization and Kinetics of its Coagulation by Endotoxin," Thromb. Diath. Haemorrh. 19:186–197 (1968). Methods of mechanical disruption of amebocytes in preparing Limulus amebocyte lysate have been described by P. A. Ward and J. H. Hill in "Detection of Lipopolysaccharide (LPS): An Improved Method for Isolation of The Limulus Extract" Proc. Soc. Exp. Biol. Med. 141:898–900 (1972) ). Methods utilizing pyrogenfree distilled water to lyse amebocyte cells in the preparation of potent amebocyte lysate have also been described. See Rojas-Corona et al., "The Limulus Coagulation Test for Endotoxin: A Comparison with Other Assay Methods," Proc. Soc. Exp. Biol. Med. 132:599–601 (1969); and J. Jorgensen et al., "Measurement of Bound and Free Endotoxin by the Limulus Assay", Proc. Soc. Exp. Biol. Med. 146:1024–1031 (1974).

In accordance with the process of the invention the Limulus amebocyte lysate is then incubated in the presence of the synthetic plastic polymer previously contacted with the biological fluid suspected of being contaminated with endotoxin. Incubation is preferably carried out at a temperature within the range of about 30° C. to about 40° C. for a time period of from about 60 to about 90 minutes. We particularly prefer to carry out incubation at about 36° C. to about 37° C., 37° C. being optimum, for about 60 to about 70 minutes.

Preferably, the synthetic plastic polymer previously contacted with the biological fluid is washed with a pyrogen-free liquid such as pyrogen-free saline prior to contacting it with the Limulus amebocyte lysate. Washing with saline is particularly preferred when whole blood is being assayed for endotoxin so as to remove any cellular material possibly adhering to the synthetic polymer.

During or after incubation the presence or absence of a gelation reaction in the Limulus amebocyte lysate is observed. The presence of a gelation reaction confirms the presence of endotoxin in the biological fluid.

As mentioned hereinbefore, the process of the invention may be employed for detecting the presence of endotoxin in substantially any type of biological fluid including parenteral fluids. Examples of parenteral fluids that may be assayed for the presence of endotoxin include saline solutions, dextrose solutions, hyperelimentation fluids, serums, plasma, albumins, and antiserums, to name a few. Moreover, the inventive process is particularly useful for detecting the presence of endotoxin in whole body and/or components of whole blood. The presence of endotoxin in whole blood and/or its components may be assayed rapidly and simply by the inventive process without any previous treatment of the blood heretofore required by previously known endotoxin assays employing Limulus amebocyte lysate.

The following examples particularly illustrate the nature of the inventive process and are not intended to be limitative thereof. The Limulus amebocyte lysate employed in the following examples was prepared by lysing amebocytes of the hemolymph of Limulus crabs obtained from the Marine Biological Laboratory, Woods Hole, Mass., with pyrogen-free distilled water in accordance with the process described by J. Jorgensen et al, supra. The amebocyte cells were lysed by the addition of pyrogen-free distilled water at a 1:3 ratio of packed cells to water. The suspension was then thoroughly mixed and allowed to stand at 4° C. for 18–24 hours. The cellular debris was then removed by centrifugation and the lysate decanted. The lysate was stored in sterile pyrogen-free polystyrene vials at −20° C. or for shorter periods of time at 4° C. until needed.

EXAMPLE I

An endotoxin standard solution was prepared by adding 10 mg endotoxin to 10 ml pyrogen-free saline (0.9% sodium chloride) to yield a solution of 1 mg/ml endotoxin concentration. The endotoxin used was a lipopolysaccharide Westphal phenol extract of *Escherichia coli* 011:B4, sold by Difco Laboratories, Detroit, Mich. This endotoxin standard solution was then diluted several times with pyrogen-free saline to provide several samples having different endotoxin concentrations. 0.1 cc of several of these samples at differing endotoxin concentrations were respectively added to 0.1 cc of Limulus amebocyte lysate for standardization of the lysate. Each of the samples with the lysate were incubated for 70 minutes at 37° C. The resultant reactions were observed and graded for degree and quality of gelation as follows:

+4 Firm clot and cloudy.
+3 Soft clot which slides down inverted tube, cloudy.
+2 High viscosity slime and cloudy.
+1 Medium viscosity and maybe cloudy.
0 Substantially clear, like water.

3.0 cc of blood was taken from a normal healthy individual. A dose of 100 units of sigma pyrogen-free heparin per cc of blood was then added to the blood sample. 1.0 cc aliquots of the heparinized blood were then placed in three pyrogen-free polystyrene tubes (Falcon Plastics, Oxnard, California). To one tube was added 0.1 cc saline (0.9% sodium chloride). 0.1 cc of 50 ng/ml endotoxin standard solution prepared previously was added to a second tube, while 0.1 cc of a 10 ng/ml endotoxin standard solution was added to the third tube. One polypropylene bead (Shell Polypropylene 5820, Shell Chemical Company, Houston, Texas) was respectively added to each tube. Each bead had an approximate diameter of about 2 mm. The contents of the three tubes were then incubated for 30 minutes at 37° C. The polypropylene beads were then removed from each tube, washed in saline and each respectively added to 0.1 cc of Limulus lysate. The Limulus lysate samples were incubated in the presence of the polypropylene beads for 70 minutes at 37° C., during which the presence or absence of a gelation reaction in the lysate was observed. The results, along with the gelation reactions of the endotoxin standard solutions, are set forth in the following Table 1.

TABLE 1

| Tube No | Content | Endotoxin Concen. ng/ml | Limulus[2] Lysate Reaction |
|---|---|---|---|
| 1 | Blood and Saline | 0 | 0 |
| 2 | Blood and Endotoxin | 50[1] | +2 |
| 3 | Blood and Endotoxin | 10[1] | +1 |
| 4 | Endotoxin Control | 100 | +4 |
| 5 | Endotoxin Control | 10 | +4 |
| 6 | Endotoxin Control | 2.5 | +3 |
| 7 | Endotoxin Control | 1 | +2 |

[1]Concentration of 0.1 cc endotoxin solution added to 1.0 blood.
[2]Lysate incubated in presence of polypropylene bead previously incubated with tube contents, except for endotoxin control solutions.

The results of Table 1 illustrate the effectiveness of the inventive process for detecting the presence of endotoxin in blood. Table 1 shows that polypropylene beads previously contacted with blood containing endotoxin (tubes 2 and 3) gave positive Limulus lysate gelation reactions while the polypropylene bead contacted with the blood and saline (tube 1) gave no reaction.

EXAMPLE II 100 ng of endotoxin (lipopolysaccharide Westphal phenol extract, E. coli 011:B4, Difco, supra) was seeded in 1.0 ml normal human serum albumin, USP 25% salt poor, (sold under the tradename METALBUMEN by Metabolic, Inc., Houston, Texas) in a pyrogen-free polystyrene tube. A 1.0 ml sample of the albumin was also added to a second pyrogen-free polystyrene tube. Two polypropylene beads (Shell Polypropylene 5820, supra), having diameters of about 2 mm, were respectively placed in each of the tubes. The samples were incubated at 37° C. for 10 minutes. The two beads were then removed, washed with pyrogen-free saline, and assayed for the presence of endotoxin by adding each bead to 0.1 ml Limulus lysate, incubating at 37° C. for 70 minutes and grading the resultant reaction for degree and quality of gelation in accordance with the Limulus Lysate Assay procedure described in Example I. Several endotoxin solutions at various concentrations were prepared by dilution of the endotoxin in saline, as described in Example I. 0.1 ml of the prepared endotoxin solutions, along with a 0.1 ml sample of the albumin were also assayed by the Limulus Lysate Assay as controls. The results of the assays are set forth in the following Table 2.

TABLE 2

| Material Assayed | Endotoxin Concentration, ng/ml | Limulus Lysate Assay Reaction |
|---|---|---|
| Endotoxin Control | 100 | +4 |
| Endotoxin Control | 10 | +4 |
| Endotoxin Control | 1 | +2 |
| Albumin Control | — | +1 |
| Polypropylene bead[1] | 100 | +4 |
| Polypropylene bead[2] | — | 0 |

[1]Bead placed in 1 ml albumin seeded with 100 ng endotoxin, incubation at 37°C. for 10 minutes. Bead washed with saline prior to assay.
[2]Bead placed in 1 ml albumin control, incubation at 37°C. for 10 minutes. Bead washed with saline prior to assay.

The results of Table 2 illustrate the effectiveness of the inventive process for detecting the presence of endotoxin in a parenteral fluid such as albumin. As shown in Table 2, endotoxin present in the albumin was adsorbed by polypropylene and incubation of the Limulus amebocyte lysate in the presence of the polypropylene bead gave a strong +4 gelation reaction in the lysate even after the polypropylene had been washed with pyrogen-free saline.

EXAMPLE III

A hemoperfusion polymer-column apparatus was designed to perform an arterial-venous shunt or by-pass to determine the effectiveness of the inventive process for detecting the presence of endotoxin in the blood of an animal. The hemoperfusion polymer-column unit was prepared by packing a sephadex gel reservoir, 5 mm diameter, 30 cm long, with 800 g. of polypropylene beads having diameters of about 2 mm, average, (Shell Polypropylene 5820, supra). The ends of the sephadex gel reservoir were covered with cotton gauze to prevent clogging. Intravenous tubes were attached to each end of the reservoir and capped with catheters. The apparatus was then attached to a dog weighing about 12 kg by injecting one catheter into an artery and the other catheter into a vein. The dog had previously been heparinized by injection with sigma pyrogen-free heparin at a dose level of about 6 units per cc of blood. The blood from the animal was removed through the arterial-intravenous line, perfused through and over the polypropylene bead column and reinfused through the venous intravenous line. The column containing the polypropylene beads was gently shaken by the use of a reciprocal shaker to prevent agglomeration of blood cells. After about 1 hour of continuous by-pass of the blood through the polymer-column no hemolysis was observed. The dog was then injected with 5 mg/kg weight endotoxin (lipopolysaccharide Westphal phenol extract of E. coli, 055:B5, Difco Laboratories, supra; reconstituted with pyrogen-free saline, 0.9% sodium chloride). Perfusion of the blood through the polymer-column was continued for 1½ hours after which the hemoperfusion apparatus was removed. The polypropylene beads in the reservoir were then washed by perfusing pyrogen-free saline through the polymer-column. One of the beads was removed from the column and added to 0.1 cc saline. 0.1 cc of the Limulus lysate standardized in Example I was then added thereto and incubated at 37° C. for 70 minutes. During incubation, a clot appeared, confirming the presence of endotoxin in the blood of the animal.

Obviously, many modifications and variations of the invention as hereinbefore set forth may be made without departing from the spirit and scope thereof, and, therefore, only such limitations should be imposed as are indicated in the appended claims.

We claim:

1. An in vitro process for determining the presence or absence of endotoxin in a biological fluid, said process comprising:
   a. contacting said biological fluid with a non-ionogenic, hydrophobic, non-polar, aliphatic, synthetic plastic polymer whereby endotoxin present in the fluid is adsorbed by the synthetic plastic polymer;
   b. removing said synthetic plastic polymer from contact with the biological fluid;
   c. contacting the plastic polymer of (b) with amebocyte lysate from the hemolymph of the horseshoe crab, *Limulus polyphemus;*
   d. incubating the amebocyte lysate in contact with the synthetic plastic polymer of (c); and
   e. observing the presence or absence of gelation reaction in the amebocyte lysate.

2. The process of claim 1 wherein said amebocyte lysate in contact with the synthetic plastic polymer of (c) is incubated at a temperature within the range of from about 30° C. to about 40° for a time period within the range of from about 60 to about 90 minutes.

3. The process of claim 1 wherein said biological fluid is blood.

4. The process of claim 3 wherein the synthetic plastic polymer previously contacted with the blood is washed with a pyrogen-free liquid prior to contact with said amebocyte lysate.

5. The process of claim 1 wherein said non-ionogenic hydrophobic non-polar aliphatic synthetic plastic polymer capable of adsorbing endotoxin is a polymer selected from the group consisting of a substantially crystalline non-polar aliphatic hydrocarbon thermoplastic polymer, a substantially crystalline non-polar aliphatic thermoplastic fluorocarbon polymer, a cross-linked aliphatic silicone elastomeric polymer and mixtures thereof, said synthetic plastic polymer being previously intimately contacted with said biological fluid whereby endotoxin present in said biological fluid is adsorbed onto the surface of said polymer.

6. The process of claim 5 wherein said synthetic plastic polymer is a poly-$\alpha$-olefin polymer.

7. The process of claim 5 wherein said synthetic plastic polymer is a thermoplastic fluorocarbon polymer.

8. The process of claim 5 wherein said synthetic plastic polymer is a cross-linked poly(alkyl-siloxane).

* * * * *